US00PP29798P3

(12) United States Plant Patent
Sidhu

(10) Patent No.: US PP29,798 P3
(45) Date of Patent: Nov. 6, 2018

(54) ***NANDINA* PLANT NAMED 'NANSID6'**

(50) Latin Name: *Nandina domestica*
Varietal Denomination: NanSid6

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 15/530,719

(22) Filed: Feb. 21, 2017

(65) Prior Publication Data

US 2017/0311505 P1 Oct. 26, 2017

(30) Foreign Application Priority Data

Apr. 26, 2016 (CA) ..... PBR 16-8903

(51) Int. Cl.
*A01H 5/00* (2018.01)
*A01H 5/12* (2018.01)

(52) U.S. Cl.
USPC ..... Plt./235
CPC ..... *A01H 5/12* (2013.01)

(58) Field of Classification Search
USPC ..... Plt./235
CPC ..... A01H 5/02; A01H 5/00
See application file for complete search history.

(56) References Cited

PUBLICATIONS http://members.tripod.com/hatch_l/orocbook3.pdf; OROC Open Registration of Cultivars International Register of Ornamental Plant Cultivars: Woody Plants: N-Z Book III: Nov. 2016; 2 pages.*

* cited by examiner

*Primary Examiner* — Kent L Bell
(74) *Attorney, Agent, or Firm* — Penny J. Aguirre

(57) ABSTRACT

A new cultivar of *Nandina domestica* named 'NanSid6' that is characterized by its foliage with new growth that is reddish purple in color and fall foliage that is red in color, its finely dissected foliage, and its compact, upright mounding habit with dense foliage.

2 Drawing Sheets

Botanical classification: *Nandina domestica.*
Variety denomination: 'NanSid6'.

CROSS REFERENCE TO A RELATED APPLICATION

This application is co-pending with a U.S. Plant Patent Application filed for a plant derived from the same breeding program that is entitled *Nandina* Plant Named 'NanSid3' (U.S. Plant patent application Ser. No. 15/530,724).

BACKGROUND OF THE INVENTION

The present invention relates to a new and distinct cultivar of *Nandina domestica* and will be referred to hereafter by its cultivar name, 'NanSid6'. 'NanSid6' is a new cultivar of heavenly bamboo shrub grown for use as a landscape plant.

The new cultivar was discovered as a branch mutation by the Inventor in 2010 in Mission, British Columbia, Canada. The new cultivar arose as a naturally occurring branch mutation of *Nandina domestica* 'Gulfstream' (U.S. Plant Pat. No. 5,656) that was growing in a container at his nursery.

Asexual reproduction of the new cultivar was first accomplished under the direction of the inventor by tissue culture of meristematic tissue in spring of 2011 in Mission, British Columbia, Canada. Asexual propagation by tissue culture and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'NanSid6' as a unique cultivar of *Nandina.*

1. 'NanSid6' exhibits foliage with new growth that is reddish purple in color and fall foliage that is red in color.
2. 'NanSid6' exhibits finely dissected foliage.
3. 'NanSid6' exhibits a compact, upright mounding habit with dense foliage.

'Gulfstream', the parent plant of 'NanSid6', is similar to 'NanSid6' in growth rate and plant habit. 'Gulfstream' differs from 'NanSid6' in having foliage with new growth that is bronzy orange in color. 'NanSid6' can be most closely compared to the cultivar 'NanSid3' and 'Sunset' (U.S. Plant Pat. No. 24,748). 'NanSid3' is similar to 'NanSid6' in growth rate and plant habit. 'NanSid3' differs from 'NanSid6' in having foliage with new growth that is more red in color and in having less finely dissected foliage. 'Sunset' is similar to 'NanSid6' in having finely divided foliage that has new growth that is purple in color. 'Sunset' differs in having foliage that is more purple in color and in having a much more open and airy plant habit.

BRIEF DESCRIPTION OF THE DRAWINGS

The accompanying colored photographs illustrate the overall appearance and distinct characteristics of two year-old plants of the new *Nandina* as grown outdoors in 1-gallon containers in St. Thomas, Ontario, Canada.

The photograph in FIG. 1 illustrates the overall plant habit and new foliage and mature foliage of 'NanSid6' in summer.

Figure 1:
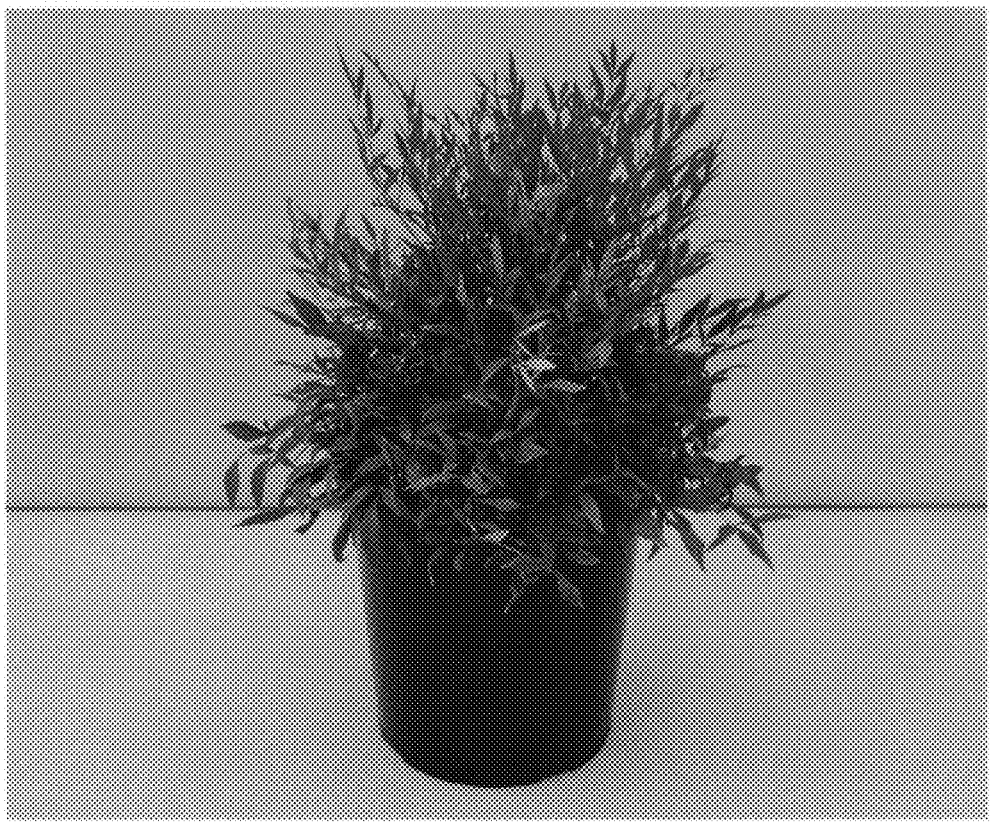
Figure 2:
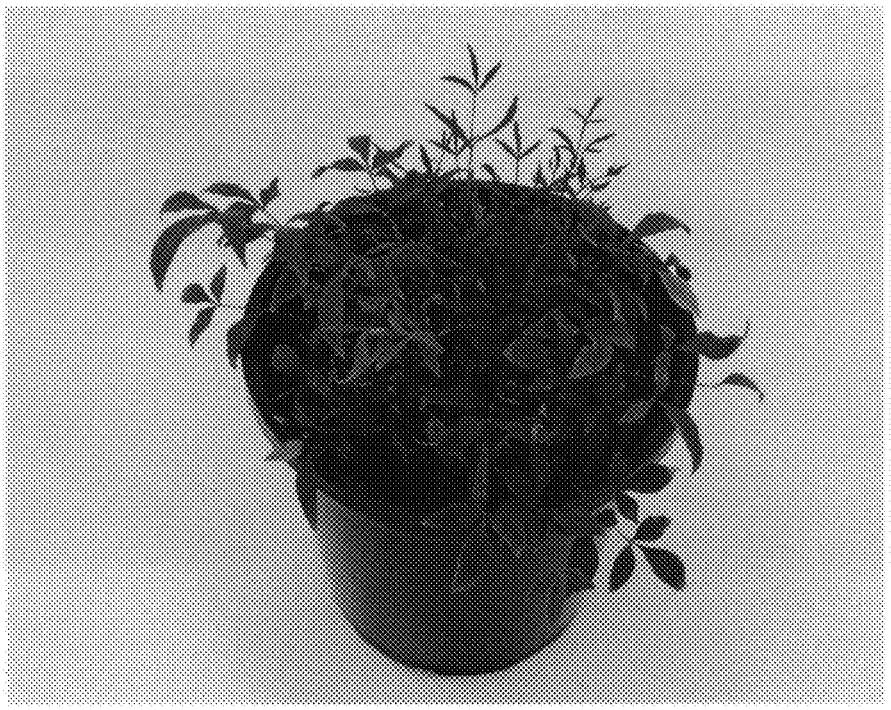

The photograph in FIG. 2 provides a view of the new foliage in spring of 'NanSid6'.

Figure 3:
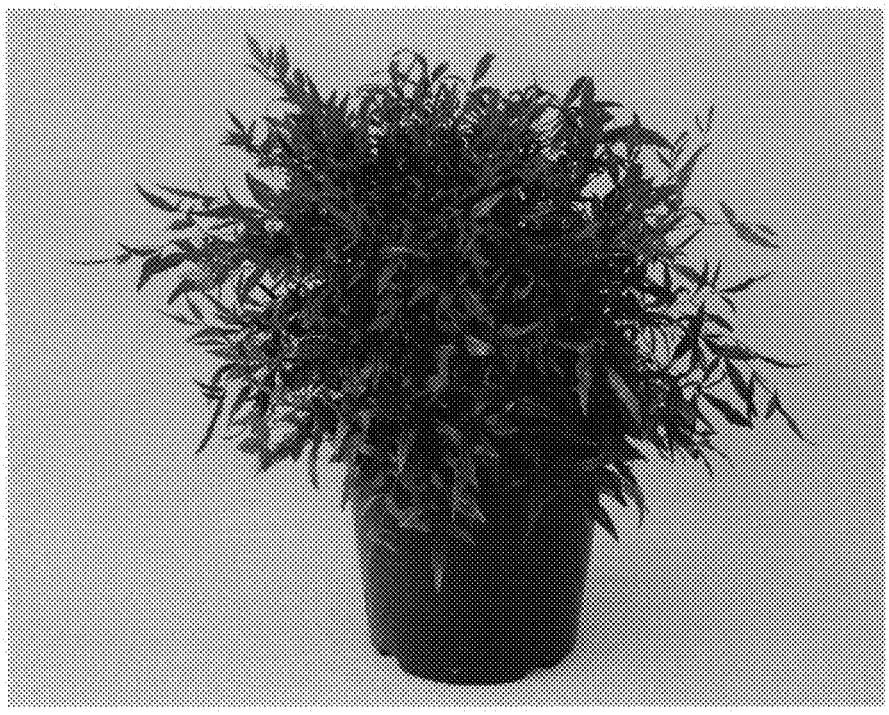

The photograph in FIG. 3 provides a view of the fall foliage of 'NanSid6'.

The colors in the photographs are as close as possible with the digital photography techniques utilized and the color values cited in the detailed botanical description accurately describe the colors of the new *Nandina*.

DETAILED BOTANICAL DESCRIPTION

The following is a detailed description of a 2 year-old plant of the new cultivar as grown outdoors in a 1-gallon container in St. Thomas, Ontario, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Evergreen to semi-evergreen shrub.

*Plant habit*.—Compact, upright mounding habit with dense foliage.

*Height and spread*.—Reaches about 28 cm in height and 31 cm in width as a 2 year-old plant in a one-gallon container and 1 m in height and 0.9 m in width in the landscape.

*Cold hardiness*.—At least in U.S.D.A. Zone 6a.

*Diseases and pests*.—No susceptibility or resistance to diseases or pests has been observed.

*Root description*.—Fibrous, outward spreading by underground rhizomes has not been observed.

*Propagation*.—Tissue culture and stem cuttings.

*Root development*.—6 to 8 weeks for a rooted cutting and about 4 months to develop a young plant from a rooted cutting.

*Growth rate*.—Moderate to slow.

Stem (cane) description:

*Stem shape*.—Rouded, comprised of clasping petioles.

*Stem strength*.—Strong.

*Stem color*.—Closest to N199A.

*Stem size*.—Average of 6.0 cm in length and 7.1 cm in width.

*Stem surface*.—Smooth.

*Stem aspect*.—Upright.

*Internode length*.—1.3 cm.

*Branching*.—Branches freely from basal buds.

Foliage description:

*Leaf shape*.—Rhomboidal.

*Leaf division*.—Mostly tri-pinnate, leaflets occur in opposite pairs, with an average of 33 leaflets per leaf.

*Leaf arrangement*.—Alternate.

*Leaf attachment*.—Petiolate.

*Leaflet base*.—Attenuate.

*Leaflet apex*.—Acute.

*Leaflet fragrance*.—None.

*Leaflet venation*.—Pinnate, not conspicuous, matches leaflet color on upper surface, mid rib is slightly protruding on lower surface.

*Leaflet margins*.—Entire.

*Leaflet surface*.—Glabrous on upper and lower surface.

*Leaflet attachment*.—Sessile.

*Leaf size*.—Average of 21.4 cm in length and 19.9 cm in width.

*Leaflet size*.—Average of 7.6 cm in length and 1.1 cm in width.

*Leaflet shape*.—Elliptic and lanceolate.

*Leaflet color*.—New growth in spring; N186C on upper surface and N186D on lower surface, as leaf expands the color gradually changes to 144A on upper surface and 144B to 144C on lower surface; summer color; outer new leaves in full sunlight close to 185A on upper surface and 185B on lower surface, mature leaves mainly N137A may be blended with 153C to 153D on upper surface and N137B on lower surface, fall color; upper leaves vary in color from 45A, 183A and 185A on upper surface and 138B suffused with 180C to 180D on lower surface, inner leaves mainly N137A on upper surface and 138B on lower surface.

*Petioles*.—Average of 4.1 cm in length and 1.2 mm in diameter, surface is glabrous and dull, clasping base 1.2 cm in length and 0.6 cm in width, color; new growth in spring; N186C, summer; outer leaves 45A, inner leaves 144B, fall; 183A on both surfaces.

*Petiolules*.—Primary; average of 3.9 cm in length and 0.5 mm in width, surface is glabrous and dull, secondary; average of 2.0 cm in length and 0.3 mm in width, surface is glabrous and dull, similar coloration as petioles.

Inflorescence description: Blooms are very rare, typically plants of the new cultivar do not bloom.

It is claimed:

1. A new and distinct cultivar of *Nandina* plant named 'NanSid6' as herein illustrated and described.

* * * * *